United States Patent [19]

Preidel et al.

[11] Patent Number: 5,458,632
[45] Date of Patent: Oct. 17, 1995

[54] IMPLANTABLE DEVICE AND MATERIALS

[75] Inventors: Walter Preidel, Erlangen, Germany; Stefanie Saeger, San Diego, Calif.

[73] Assignee: Pacesetter AB, Solna, Sweden

[21] Appl. No.: 99,990

[22] Filed: Jul. 30, 1993

Related U.S. Application Data

[63] Continuation of Ser. No. 738,875, Aug. 1, 1991, abandoned.

[30] Foreign Application Priority Data

Aug. 10, 1990 [DE] Germany .......................... 40 25 438.0

[51] Int. Cl.⁶ ......................................................... A61N 1/05
[52] U.S. Cl. ................................................. 607/121; 607/120
[58] Field of Search ............................... 623/1; 607/120, 607/121; 128/DIG. 22

[56] References Cited

U.S. PATENT DOCUMENTS

| | | | |
|---|---|---|---|
| 3,639,141 | 2/1972 | Dyck . | |
| 4,033,357 | 7/1977 | Helland et al. | 128/419 P |
| 4,495,934 | 1/1985 | Shaw, Jr. | 128/833 |
| 4,506,680 | 3/1985 | Stokes | 607/120 |
| 4,678,660 | 7/1987 | McGary et al. | 128/DIG. 22 |
| 4,749,585 | 6/1988 | Greco et al. | 427/2 |
| 4,906,465 | 3/1990 | Chaikof et al. | 623/1 |
| 5,053,008 | 10/1991 | Bajaj | 128/24 AA |
| 5,053,048 | 10/1991 | Pinchuk | 128/DIG. 21 |

FOREIGN PATENT DOCUMENTS

| | | |
|---|---|---|
| 0338418 | 10/1989 | European Pat. Off. . |
| 0388480 | 9/1990 | European Pat. Off. . |
| WO90/00343 | 1/1990 | WIPO . |
| WO90/01305 | 2/1990 | WIPO . |

*Primary Examiner*—William E. Kamm
*Assistant Examiner*—Kennedy J. Schaetzle
*Attorney, Agent, or Firm*—Kenyon & Kenyon

[57] ABSTRACT

The invention relates to implantable devices and materials, in which at least one part of the surface is provided with a tissue-plasminogen activator (t-PA). In this way, inflammatory reactions of the body and the formation of fibrous capsules, which ordinarily occur after implantation, are avoided or reduced.

5 Claims, No Drawings

IMPLANTABLE DEVICE AND MATERIALS

This application is a continuation, of application Ser. No. 07/738,875 filed Aug. 1, 1991, now abandoned.

BACKGROUND OF THE INVENTION

1. Field of the Invention

The invention relates to body implantable devices and materials.

2. Description of Related Art

When devices or materials are implanted in an organism, the body's own immune system starts a defense reaction as soon as the implant is recognized as foreign. Since during an implantation, the surrounding tissue is usually damaged, injured or considerably altered, additional bleeding occurs causing thrombi [blood clots] to be formed. The disintegration of these thrombi then initiates the formation of connective tissue. The thickness of the connective tissue layer depends on the biocompatibility of the implant and on the extent of trauma to the surrounding tissue.

The thickness of connective tissue layers could be diminished by reducing the formation of thrombi or by causing them to disintegrate. Thus, one could improve the functioning of implants whose operativeness is adversely affected by connective tissue. For example, in the case of stimulating electrodes for pacemakers, attempts have been made to reduce the defense reaction of the body, that is the formation of connective tissue layers by using asteroid such as Cortisone or Dexamethasone (c.f.: U.S. Pat. No. 5,103,837). However, these medicines are not specifically effective with regard to the formation of thrombi and the reduction of connective tissue growth; an overdose could even cause unwanted side effects.

The object of the invention is to provide body implantable devices and materials wherein the formation of thrombi and connective tissue is prevented or reduced in connection with the implantation thereof.

SUMMARY OF THE INVENTION

In accordance with the invention, at least one part of the surface of the implantable devices or materials is provided with a tissue-plasminogen activator. The tissue-plasminogen activator which is applied functions as a fibrinolytic substance.

DETAILED DESCRIPTION OF THE INVENTION

The tissue-plasminogen activator (t-PA), which has good water-solubility properties, is a proteolytic protein molecule (with a complicated tertiary structure). As an endogenous substance, t-PA has no antigenic effect whatsoever. t-PA is produced in the body by the endothelium cells in the heart, liver and kidneys; it can be extracted in its completely pure form using genetic engineering means. t-PA is available commercially as a dry substance. The lyophilized powder can be stored at room temperature for about 18 months; in dissolved form, its storage stability [non-perishability] is about 8 h (in cool storage about 24 h).

For some time, the agent t-PA has been used in medicine for heart attack therapy; its purpose is to reopen closed vessels, that is to break up thrombi. In accordance with the invention, t-PA can now be used to prevent rejection reactions when devices or materials are implanted. By applying t-PA to the surface of devices and materials to be implanted, one can reduce the body's inflammatory reactions and the formation of fibrous capsules.

The invention offers the following possible particular applications:
— Surfaces of implants placed in the blood circulation or tissue
— Pacemaker housings
— Pacemaker electrodes
— Catheters for insulin pumps
— Sensor surfaces in blood or tissue
— Membranes.

A preferred goal of the invention is to prevent connective tissue from being formed from the thrombi, which develop when stimulating electrodes for pacemakers are implanted. In principle, however, t-PA can be applied to any implantable devices and materials. Blood or lymph fluid causes t-PA to be separated from the implants, so that it can then break up the thrombi which form on the implant. An advantageous feature is that the plasminogen activator is only active in the presence of fibrin, that is when blood clots are formed, and otherwise does not interfere with physiological processes.

The following mechanism is the basis of the fibrinolytic action of the tissue-plasminogen activator. First, t-PA bonds to a fibrin clot; then plasminogen bonds to t-PA. The hydrolysis of a peptide bond causes the plasminogen to be subsequently split to form active plasmin, through which means the fibrin clot is broken down into fibrin cleavage products. The crucial property of t-PA is its fibrin specificity. Together with fibrin and plasminogen, the tissue-plasminogen activator forms a complex, and thus activates only fibrin-bonded plasminogen. In the remaining vascular system, t-PA remains largely inactive; if there is no blood clot, then t-PA is inactivated by means of inhibitors.

As is true of all proteins, t-PA is not heat or radiation resistant, and is also not resistant to ethylene oxide. For that reason, t-PA can only be effectively applied to the devices and materials to be implanted after they have been sterilized, for example shortly before they are implanted. The quantity of t-PA required in the case of the subject matter of the invention for the thrombolytic effect lies within the scope of the therapeutic measures used in heart attack therapy. In this connection, the dose of 1 mg t-PA per kilogram of body weight has proven to be effective.

EXAMPLE

The invention shall be clarified in still greater detail on the basis of exemplified embodiments relating to the effectiveness of t-PA, that is its thrombolytic activity. For this purpose, thrombi were produced in vitro and the quantity of t-PA needed to break them up was determined. Moreover, to simulate the marginal conditions present during an implantation, various quantities of t-PA were applied to the surface of a stimulating electrode made of glassy carbon. This system was then tested in an in-vitro experiment using flowing fresh blood.

1 ml fresh, venous blood was injected into a silicon tube (tube length: 25 cm; interior diameter: 0.4 cm), whose extremities are closed to form a ring; the blood column filled the tube to about one third. The blood was coagulated by rotating the tube on a rotatable disk. A thrombus about 1 cm × 0.4 cm large is formed thereby and occludes the tube lumen. It is very similar in its structure to an in-vivo thrombus The thrombolytic activity on the thrombi produced in vitro in the manner described above was determined by injecting varying volumes of a solution of 50 μg t-PA in sterile, bidistilled water into the tube. It turned out that the total concentration of t-PA required to disintegrate a thrombus amounted to about 1 μg/ml of blood. Adding about 5 μg t-PA/ml immediately to the blood prevented a thrombus from forming.

Glassy carbon electrodes (surface: 0.125 cm$^2$; volume porosity: 50%) cleaned in isopropanol and acetone were incubated with aqueous solutions of t-PA for 20 h at room temperature under sterile conditions; thereby an adsorption of t-PA on the electrode surface occured. The electrodes were subsequently introduced through a T-shape connecting tube into a tubular system of the type described above and subjected to the rotating blood column. It turned out that a blood clot did not form, that is to say developing coagulates were immediately dissolved again. A quantity of a few μg t-PA was enough to prevent thrombi from forming.

What is claimed is:

1. An article which is implantable in a human body having a surface, at least a portion of said surface having a tissue-plasminogen activator adsorbed directly thereon, the tissue-plasminogen activator being directly adsorbed into the surface without being chemically bonded to any polymer on the surface and without being bonded to the surface, and said adsorbed tissue-plasminogen activator being releasable and detachable from the surface of the article upon implantation in the body and upon contact with blood or lymph fluid.

2. The article according to claim 1 wherein the article is a pacemaker having at least one electrode and wherein the tissue-plasminogen activator is adsorbed into a surface of the at least one electrode.

3. The article according to claim 1 wherein the article is a pacemaker having a housing and wherein the tissue-plasminogen plasminogen activator is adsorbed into an outer surface of said housing.

4. The article according to claim 1 wherein the article is a catheter.

5. The article according to claim 1 wherein the article is a stimulating electrode of a pacemaker.

* * * * *

UNITED STATES PATENT AND TRADEMARK OFFICE
CERTIFICATE OF CORRECTION

PATENT No. : 5,458,632

DATED : October 17, 1995

INVENTOR(S): Walter Preidel et al.

It is certified that error appears in the above-identified patent and that said Letters Patent is hereby corrected as shown below:

On the title page,
Item [54] "DEVICE" should be --DEVICES--;

Column 1, line 1, "DEVICE" should be --DEVICES--;

Column 1, line 29, "asteroid" should be --a steroid--;

Column 4, line 14, second occurrence, delete "plasminogen".

Signed and Sealed this

Tenth Day of September, 1996

BRUCE LEHMAN

*Attest:*

*Attesting Officer*  *Commissioner of Patents and Trademarks*